United States Patent
Souchaud et al.

(10) Patent No.: US 12,175,663 B2
(45) Date of Patent: Dec. 24, 2024

(54) DEVICE AND METHOD FOR PRODUCING A DIGITAL VIDEO CLASSIFIER

(71) Applicants: ASSISTANCE PUBLIQUE-HOPITAUX DE PARIS, Paris (FR); SORBONNE UNIVERSITE, Paris (FR); CENTRE NATIONAL DE LA RECHERCHE SCIENTIFIQUE, Paris (FR); ÉCOLE NATIONALE SUPÉRIEURE DE L'ELECTRONIQUE ET DE SES APPLICATIONS, Cergy (FR); CY ENERGY PARIS UNIVERSITÉ, Cergy (FR)

(72) Inventors: Marc Souchaud, Cergy (FR); Aymeric Histace, Menucourt (FR); Romain Leenhardt, Paris (FR); Xavier Dray, Paris (FR)

(73) Assignees: ASSISTANCE PUBLIQUE-HOPITAUX DE PARIS, Paris (FR); SORBONNE UNIVERSITE, Paris (FR); CENTRE NATIONAL DE LA RECHERCHE SCIENTIFIQUE, Paris (FR); ÉCOLE NATIONALE SUPÉRIEURE DE L'ELECTRONIQUE ET DE SES APPLICATIONS, Cergy (FR); CY CERGY PARIS UNIVERSITE, Cergy (FR)

( * ) Notice: Subject to any disclaimer, the term of this patent is extended or adjusted under 35 U.S.C. 154(b) by 293 days.

(21) Appl. No.: 17/487,070

(22) Filed: Sep. 28, 2021

(65) Prior Publication Data

US 2022/0101525 A1 Mar. 31, 2022

(30) Foreign Application Priority Data

Sep. 30, 2020 (EP) .................................. 20306140

(51) Int. Cl.
*G06T 7/00* (2017.01)
*G06F 16/55* (2019.01)
(Continued)

(52) U.S. Cl.
CPC ............ *G06T 7/0012* (2013.01); *G06F 16/55* (2019.01); *G06F 16/75* (2019.01); *G06N 3/08* (2013.01);
(Continued)

(58) Field of Classification Search
CPC ......... G06T 7/0012; G06T 2207/10016; G06T 2207/10068; G06T 2207/30028;
(Continued)

(56) References Cited

U.S. PATENT DOCUMENTS 10,980,404 B2 4/2021 Dray et al.
2012/0316421 A1 12/2012 Kumar et al.

FOREIGN PATENT DOCUMENTS

CN 110916606 A 3/2020
EP 3539455 A1 9/2019
(Continued)

OTHER PUBLICATIONS

Buijs, M.M., Ramezani, M.H., Herp, J., Kroijer, R., Kobaek-Larsen, M., Baatrup, G. and Nadimi, E.S., 2018. Assessment of bowel cleansing quality in colon capsule endoscopy using machine learning: a pilot study. Endoscopy international open, 6(08), pp. E1044-E1050.*

(Continued)

*Primary Examiner* — Zhitong Chen
(74) *Attorney, Agent, or Firm* — Tucker Ellis LLP

(57) ABSTRACT

The present invention concerns a device for producing a "digital video classifier" configured to determine the quality of cleanliness of one or more segments of the digestive tube in a video capsule endoscopy (VCE) of a subject, compris- (Continued)

ing: a VCE allowing the acquisition of videos of segments of the digestive tube, video storage means, coupled with the VCE, an "image database" with images extracted from VCE exams, a "video database" with videos extracted from VCE exams, calculating means connected to the video storage means, and to the databases, and configured for performing a statistical learning for the generation of a "digital image classifier" from the "image database" and which classifies the images in adequate cleanliness or non-adequate cleanliness; generating the "digital video classifier" capable of classifying a video of a subject as being of adequate cleanliness or of non-adequate cleanliness of one or more segments of the digestive tube.

14 Claims, 4 Drawing Sheets

(51) Int. Cl.
| | | |
|---|---|---|
| *G06F 16/75* | (2019.01) | |
| *G06N 3/08* | (2023.01) | |
| *G06V 20/40* | (2022.01) | |
| *G16H 30/20* | (2018.01) | |
| *A61B 1/00* | (2006.01) | |
| *A61B 1/04* | (2006.01) | |
| *G06V 10/94* | (2022.01) | |

(52) U.S. Cl.
CPC ............ *G06V 20/41* (2022.01); *G16H 30/20* (2018.01); *A61B 1/00009* (2013.01); *A61B 1/041* (2013.01); *G06T 2207/10016* (2013.01); *G06T 2207/10068* (2013.01); *G06T 2207/30028* (2013.01); *G06V 10/95* (2022.01); *G06V 2201/031* (2022.01)

(58) Field of Classification Search
CPC ........... G06T 2207/20081; G06T 2207/20084; G06T 7/0014; G06F 16/55; G06F 16/75; G06N 3/08; G06V 20/41; G06V 10/95; G06V 2201/031; G06V 10/454; G06V 10/764; G06V 20/40; G16H 30/20; A61B 1/00009; A61B 1/041; A61B 1/000096
See application file for complete search history.

(56) References Cited

FOREIGN PATENT DOCUMENTS

| | | | | |
|---|---|---|---|---|
| FR | 3539455 A1 | * | 9/2019 | ............ A61B 1/04 |
| WO | 2020079696 A1 | | 4/2020 | |

OTHER PUBLICATIONS

Li, P., Li, Z., Gao, F., Wan, L. and Yu, J., Jul. 2017. Convolutional neural networks for intestinal hemorrhage detection in wireless capsule endoscopy images. In 2017 IEEE International Conference on Multimedia and Expo (ICME) (pp. 1518-1523). IEEE.*
Noorda, R., Nevárez, A., Colomer, A., Naranjo, V. and Beltrán, V.P., May 2019. Automatic detection of intestinal content to evaluate visibility in capsule endoscopy. In 2019 13th International Symposium on Medical Information and Communication Technology (ISMICT) (pp. 1-6). IEEE.*
European Search Report in EP 20306140.3 dated Feb. 25, 2021, 12 pages.
Enns, et al. "Clinical Practice Guidelines for the Use of Video Capsule Endoscopy." Gastroenterology 2017; vol. 152, No. 3. pp. 497-514.
Hicks, et al. "Dissecting Deep Neural Networks for Better Medical Image Classification and Classification Understanding." 2018 IEEE 31st International Symposium on Computer-Based Medical Systems. Jun. 18, 2018. pp. 363-368.
Brotz, et al. "A validation study of 3 grading systems to evaluate small-bowel cleansing for wireless capsule endoscopy: a quantitative index a qualitative evaluation, and an overall adequacy assessment." Gastrointestinal Endoscopy. vol. 69. No. 2. 2009. 10 pages.
Hong-Bin, et al. "Evaluation of Visualized Area Percentage Assessment of Cleansing Score and Computed Assessment of Cleansing Score for Capsule Endoscopy." The Saudi Journal of Gastroenterology. vol. 19. No. 4. Jan. 2013. 5 pages.
Iddan, et al. "Wireless capsule endoscopy." Nature. vol. 405. May 25, 2000. pp. 417-418.
Le Berre, et al. "Reviews in Basic and Clinical Gastroenterology and Hepatology: Application of Artificial Intelligence to Gastroenterology and Hepatology." Gastroenterology 2020. vol. 158. pp. 76-94.
Niv, Yaron. "Efficiency of bowel preparation for capsule endoscopy examination: A meta-analysis." World Journal of Gastroenterology. Mar. 7, 2008. vol 14. No. 9. pp. 1313-1317.
Rajkomar, et al. "Machine Learning in Medicine." The New England Journal of Medicine. vol. 380. No. 14. Apr. 4, 2019. pp. 1347-1358.
Simonyan, et al. "Very Deep Convolutional Networks for Large-Scale Image Recognition." Published as a conference paper at ICLR 2015. 14 pages.
Spada, et al. "Performance measures for small-bowel endoscopy: A European Society of Gastrointestinal Endoscopy (ESGE) Quality Improvement Initiative." United European Gastroenterology Journal. May 2019. vol. 7. No. 5. pp. 614-641.
Weyenberg, et al. "Description of a novel grading system to assess the quality of bowel preparation in video capsule endoscopy." Endoscopy. Mar. 2011. 7 pages.
Abou Ali Einas et al. "Development and validation of a computed assessment of cleansing score for evaluation of quality of small-bowel visualization in capsule endoscopy." Endoscopy International Open, vol. 6, No. 6, May 2018, pp. E646-E651.

* cited by examiner

ROC curve obtained on the training subset of the videodatabase.

ROC curve obtained on the testing subset of the image database for the validation of the NN-algorithm.

| Video number | Proportion of images beyond which each video is considered adequate (Algo IA) | video ground truth | Threshold 1 (>10% -> Adequate) | Category (Positive -> Adequate) | Threshold 2 (>40% -> Adequate) | Category (Positive -> Adequate) | Threshold 3 (>70% -> Adequate) | Category (Positive -> Adequate) |
|---|---|---|---|---|---|---|---|---|
| 1 | 55% | Not Adequate | Adequate | False Positive | Adequate | False Positive | Not Adequate | True Negative |
| 2 | 76% | Adequate | Adequate | True Positive | Adequate | True Positive | Adequate | True Positive |
| 3 | 20% | Not Adequate | Adequate | False Positive | Not Adequate | True Negative | Not Adequate | False Negative |
| 4 | 45% | Adequate | Adequate | True Positive | Adequate | True Positive | Not Adequatee | False Negative |
| 5 | 86% | Adequate | Adequate | True Positive | Adequate | True Positive | Adequate | True Positive |
| Sensitivity (TP/(TP+FN) | | | | 100% | | 100% | | 50% |
| Specificity TN/(TN+FP) | | | | 0% | | 50% | | 100% |

Figure 4

DEVICE AND METHOD FOR PRODUCING A DIGITAL VIDEO CLASSIFIER

FIELD OF THE INVENTION

The invention concerns a device for producing a "digital video classifier" in order to determine the quality of cleanliness of one or more segments of the digestive tube in a video capsule endoscopy (VCE) of a subject.

STATE OF ART

Artificial intelligence (AI) has started its conquest of the healthcare and medical world, including gastroenterological endoscopy. AI can be used for screening, diagnosis, characterization, treatment, and prognosis evaluation, in a wide array of procedures, and especially in Capsule endoscopy and in small bowel capsule endoscopy (SBCE).

Capsule endoscopy (CE) has become the mainstay of small bowel (SB) examination over the last 20 years (1). SBCE systems have no cleansing or suctioning capabilities. Bile, bubbles, residues and liquids can alter the visualization of the SB mucosa, and they possibly decrease the diagnostic performance of SBCE examinations. Several cleanliness scores have been proposed for SBCE, but none have been subjected to external validation (2). Among others scores, the three different scores for the evaluation of SB cleanliness during CE proposed by Brotz et al. initially received praise because the authors claimed that all three scores had been validated (3). Nevertheless, these scores had poor interobserver reproducibility coefficients, which has been confirmed recently in an external (un)validation study (4). Overall, although the use of a cleanliness score is recommended for SBCE (5,6) no reliable and fully validated scale is available for clinical practice. Moreover, in the absence of validated cleanliness scores, any assessment or comparison of SBCE preparation regimens remains challenging. The European Society for Gastrointestinal Endoscopy (ESGE) and United European Gastroenterology (UEG) have recently called for "the development of software for assessment of the quality of SB preparation" (5).

INVENTION

The aim of this invention is to develop a video classifier, such as a neural network (NN)-based algorithm, for automated assessment of the SB cleanliness during CE.

SUMMARY OF THE INVENTION

The following sets forth a simplified summary of selected aspects, embodiments and examples of the present invention for the purpose of providing a basic understanding of the invention. However, the summary does not constitute an extensive overview of all the aspects, embodiments and examples of the invention. The sole purpose of the summary is to present selected aspects, embodiments and examples of the invention in a concise form as an introduction to the more detailed description of the aspects, embodiments and examples of the invention that follow the summary.

Here, the invention presents a device for producing a digital video classifier configured to determine the quality of cleanliness of one or more segments of the digestive tube of a subject from a capsule endoscopy video of the subject digestive tube, comprising:

a data storage medium configured to store:
- an "image database" with images extracted from video capsule endoscopy—VCE—exams and categorized into predetermined images categories including images with "adequate" cleanliness and images with "non-adequate" cleanliness; preferably said predetermined image categories referring to a score determined by a visual analysis of the images based on at least one medical criteria, and
- a "video database" with videos extracted from VCE exams categorized into predetermined video categories including videos with "adequate" cleanliness and videos with "non-adequate" cleanliness; preferably said predetermined video categories referring to a score determined by a visual analysis of the videos based on at least one medical criteria, the medical criteria being elaborated notably from items selected from: percentage of mucosa visualized, luminosity, presence of bubbles, presence of bile/chyme, presence of liquids and/or undigested debris, one or several processors connected to the data storage medium, and configured for:
(A) performing a statistical learning for the generation of a "digital image classifier" from the "image database" and which classifies the images in adequate cleanliness or non-adequate cleanliness;
(B) generating the "digital video classifier", by the following steps:
a) extraction of all the successive images of each video from the "video database";
b) automatic classification of the quality of all the successive images from each extracted video, in adequate cleanliness or non-adequate cleanliness, by the "digital image classifier", and computing a "video cleanliness score" for each video according to the proportion of images whose quality is of adequate cleanliness;
c) automatic classifications of the videos into video with "adequate" cleanliness and videos with "non-adequate" cleanliness, each of said classifications of the videos being done with one of a plurality of threshold values applied to the video cleanliness score;
d) computing a plurality of receiver operating characteristic—ROC—for each of the automatic classifications of the videos according to the predetermined video categories;
e) computing of a desired threshold value between 0% and 100% of the video cleanliness score allowing to obtain desired values in terms of ROC performance, the value of this desired threshold of the video cleanliness score becoming, in combination with the digital image classifier, the "digital video classifier" capable of classifying a video of one or more segments of a subject digestive tube as being of adequate cleanliness or of non-adequate cleanliness.

Such a method allows the production of a digital video classifier which can be used for automated assessment of the SB cleanliness based on CE video. This invention paves the way for automated, standardized small bowel capsule endoscopy reports. The use of predetermined video or image categories, preferably from a consensual classification by expert readers provided a strong asset for the assessment of SB cleanliness. Such a digital video classifier was evaluated on a random subset of 78 videos with the experts' consensual classification ("adequate" vs. "inadequate") of cleanliness as a reference and it proved to be highly sensitive and also specific.

According to other optional features of the device:

the one or several processors are also configured for f) validating the desired threshold of the video cleanliness score with another set of videos from the "video database". This will confirm the sensitivity and specificity of the classifier.

the step f) comprises a validation of the desired threshold by comparison of the receiver operating characteristic, such as values of sensitivity and specificity, obtained with a first subset of videos with the receiver operating characteristic obtained with a second subset of videos.

the validation of the "digital video classifier" is realized in the step f), when the variation of obtained receiver operating characteristic such as values of sensitivity and specificity is 2% maximum between the second subset of videos and the first subset of videos, for the desired threshold.

in step f) the two subsets of the "video database" are selected so as to have the same proportions of adequate cleanliness/non-adequate cleanliness videos according to the predetermined video categories.

in step f) both subsets of the "video database" have the same size.

in step f), both subsets of the "video database" are produced randomly.

the computing a plurality of ROCs in the steps c) and d) comprises the following sub-steps:
  variation between 0% and 100%, of the plurality of threshold values applied to the video cleanliness score corresponding to the proportion of images beyond which each video is considered adequate,
  labeling of each video in a subset as "adequate cleanliness video" or "not adequate cleanliness video" depending on the threshold values,
  for each given threshold value, counting the number of False Positives, True Positives, False Negatives and True Negatives in the videos of the first subset, by comparison of the video labels with the predetermined videos categories, to determine associated values of receiver operating characteristic (e.g. sensitivity, 1-specificity) associated with the given threshold value, and
  plotting a ROC curve from the set of values obtained for each threshold value.

This will enhance the sensitivity and specificity of the classifier.

the receiver operating characteristic includes, preferably corresponds to true positive rate and false positive rate at various threshold settings.

the calculating means are configured to perform, in the step (A), a statistical learning for the generation of a "digital image classifier" from the "image database" comprising:
  (i) a step of automatic learning according to the technique known as "deep neural networks" on a subset of the "image database" drawn at random, allowing the generation of a "digital image classifier", and
  (ii) a test step on the remaining images of the "image database" enabling the specificity and sensitivity of the "digital image classifier" to be validated, by comparison of the automatic classification with the predetermined image categories of these remaining images.

the "digital image classifier" is validated when at least the tested images have a specificity and a sensitivity at least equal to 90% compared to the predetermined image categories.

in step (A) learning is realized by a deep neural network architecture of the "Convolutional Neural Network (CNN)" type or of the "Generative Adversarial Network (GAN)" type.

According to another aspect of the present invention, it is provided a method for producing a digital video classifier configured to determine the quality of cleanliness of one or more segments of the digestive tube of a subject from a capsule endoscopy video of the subject digestive tube, said method being executed by one or several processors connected to a data storage medium configured to store:

an "image database" with images extracted from video capsule endoscopy—VCE—exams and categorized into predetermined images categories including images with "adequate" cleanliness and images with "non-adequate" cleanliness; preferably said predetermined image categories referring to a score determined by a visual analysis of the images based on at least one medical criteria, and a "video database" with videos extracted from VCE exams categorized into predetermined video categories including videos with "adequate" cleanliness and videos with "non-adequate" cleanliness; preferably said predetermined video categories referring to a score determined by a visual analysis of the videos based on at least one medical criteria, the medical criteria being elaborated from items selected from: percentage of mucosa visualized, luminosity, presence of bubbles, presence of bile/chyme, presence of liquids and undigested debris, said method comprising the following steps:
  (A) performing a statistical learning for the generation of a "digital image classifier" from the "image database" and which classifies the images in adequate cleanliness or non-adequate cleanliness;
  (B) generating the "digital video classifier", by the following steps:
    a) extraction of all the successive images of each video from the "video database";
    b) automatic classification of the quality of all the successive images from each extracted video, in adequate cleanliness or non-adequate cleanliness, by the "digital image classifier", and computing a "video cleanliness score" for each video according to the proportion of images whose quality is of adequate cleanliness;
    c) automatic classifications of the videos into video with "adequate" cleanliness and videos with "non-adequate" cleanliness, each of said classifications of the videos being done with one of a plurality of threshold values applied to the video cleanliness score;
    d) computing a plurality of receiver operating characteristic—ROC—for each of the automatic classifications of the videos according to the predetermined video categories;
    e) computing of a desired threshold value between 0% and 100% of the video cleanliness score allowing to obtain desired values in terms of ROC performance,
  the value of this desired threshold of the video cleanliness score becoming, in combination with the digital image classifier, the "digital video classifier" capable of classifying a video of one or more segments of a subject digestive tube as being of adequate cleanliness or of non-adequate cleanliness.

According to other optional features of the method:
the steps c) and d) comprises the following sub-steps:
- variation between 0% and 100%, of the plurality of threshold values applied to the video cleanliness score corresponding to the proportion of images beyond which each video is considered adequate,
- labeling of each video in a subset as "adequate cleanliness video" or "not adequate cleanliness video" depending on the threshold values,
- for each given threshold value, counting the number of False Positives, True Positives, False Negatives and True Negatives in the videos of the first subset, by comparison of the video labels with the predetermined videos categories, to determine associated values of receiver operating characteristic (e.g. sensitivity, 1-specificity) associated with the given threshold value,
- plotting a ROC curve from the set of values obtained for each threshold value.

it also comprises a step of:
- f) validating the desired threshold of the video cleanliness score with another set of videos from the "video database".

it also comprises a step of:
- a step of automatic learning according to the technique known as "deep neural networks" on a subset of the "image database" drawn at random, allowing the generation of a classifier known as the "digital image classifier",
- a test step on the remaining images of the "image database" enabling the specificity and sensitivity of the "digital image classifier" to be validated, by comparison with the predetermined image categories of these images.

in step (A) learning is realized by a deep neural network architecture of the "Convolutional Neural Network (CNN)" type or of the "Generative Adversarial Network (GAN)" type.

According to another aspect of the present invention, it is provided a method of control applied to a given video made by video capsule, in at least one segment of the digestive tube of a person, for automatically determining the quality of visualization of the images of the video, said method
- using the "digital video classifier" according to the invention applied to the given video,
- to automatically determine, in an automatic screening test, whether the video given is of "adequate" or "non-adequate" cleanliness.

In particular the method of control according to the invention, applied to different persons, characterized in that the method has:
- a preliminary step of non-chirurgical intestinal preparation for the control examination, which is different for each person,
- a step of controlling the automatic examination of the video carried out on each person,
- a step of comparing the efficiency of the different intestinal preparations under examination according to the video cleanliness score obtained from each video, determined for each different intestinal preparation by the method of control.

According to another aspect of the present invention, it is provided a device for the automated assessment of the small bowel cleanliness based on capsule endoscopy video, said device comprising one or several processor configured to apply the "digital video classifier" produced according to the invention to a given video made by endoscopy video capsule, and to automatically determine whether the video given is of "adequate" or "non-adequate" cleanliness.

Such a determination is based for example on at least one segment of the digestive tube of a person and can be done from a score generated by the digital video classifier" according to the invention.

BRIEF DESCRIPTION OF THE DRAWINGS

Other advantages and characteristics of the disclosed devices and methods will become apparent from reading the description, illustrated by the following figures, where:

FIG. 4: An example of the invention

DETAILED DESCRIPTION

Figure 1:
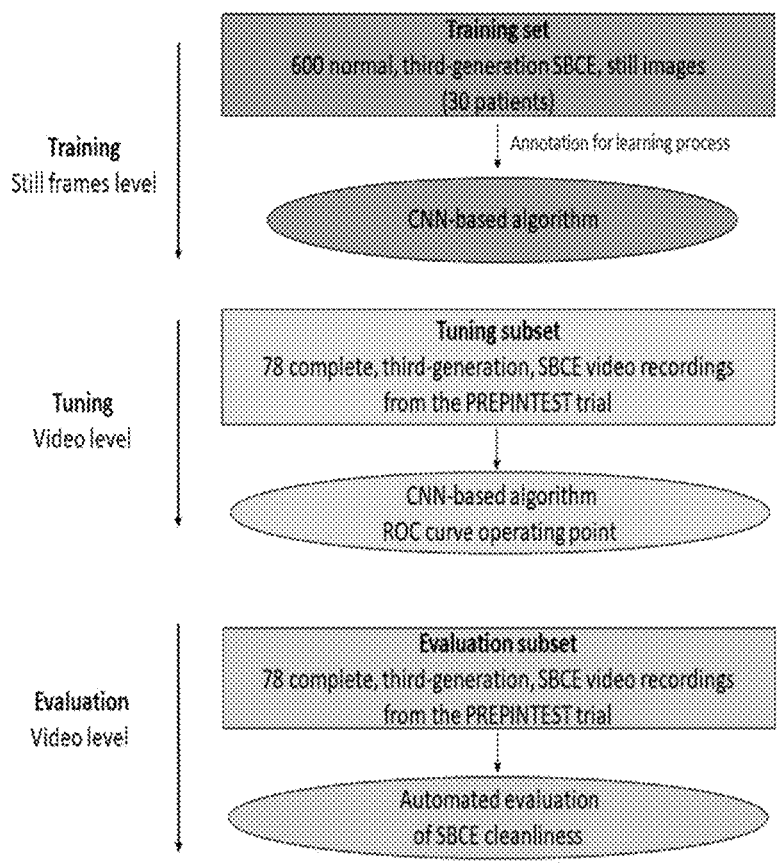
FIG. 1: Study flowchart of an example of the invention
Figure 2:
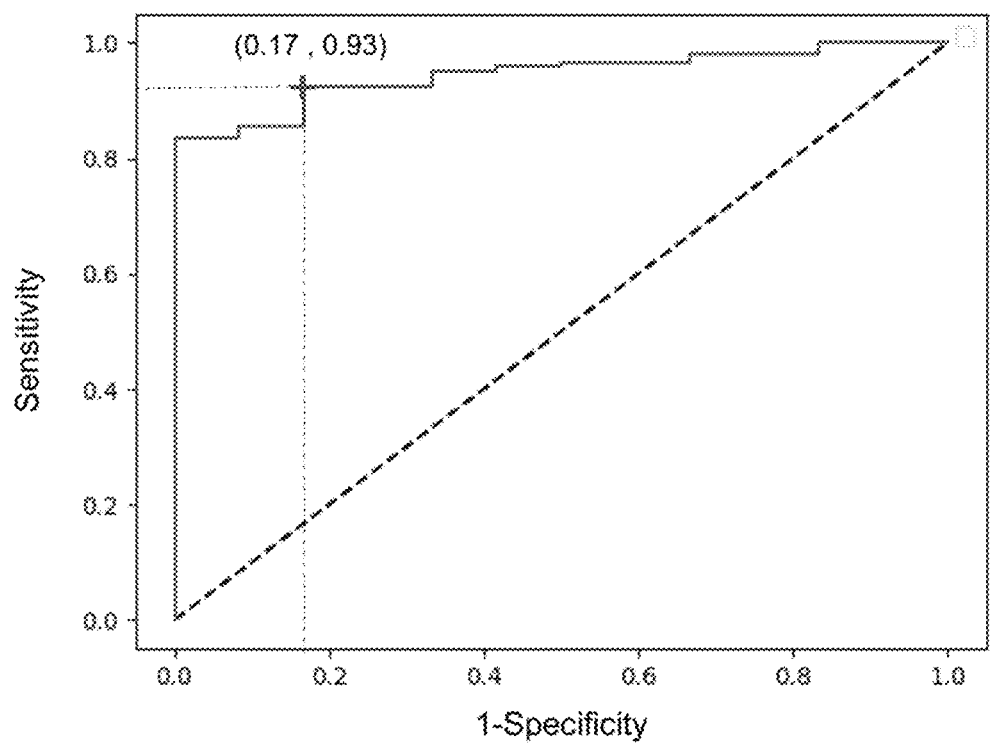
FIG. 2: Receiver operating characteristic (ROC) curve from the comparison of the outputs of an NN-based algorithm to the experts' evaluation on the learning subset, so as to validate the digital image classifier.
Figure 3:
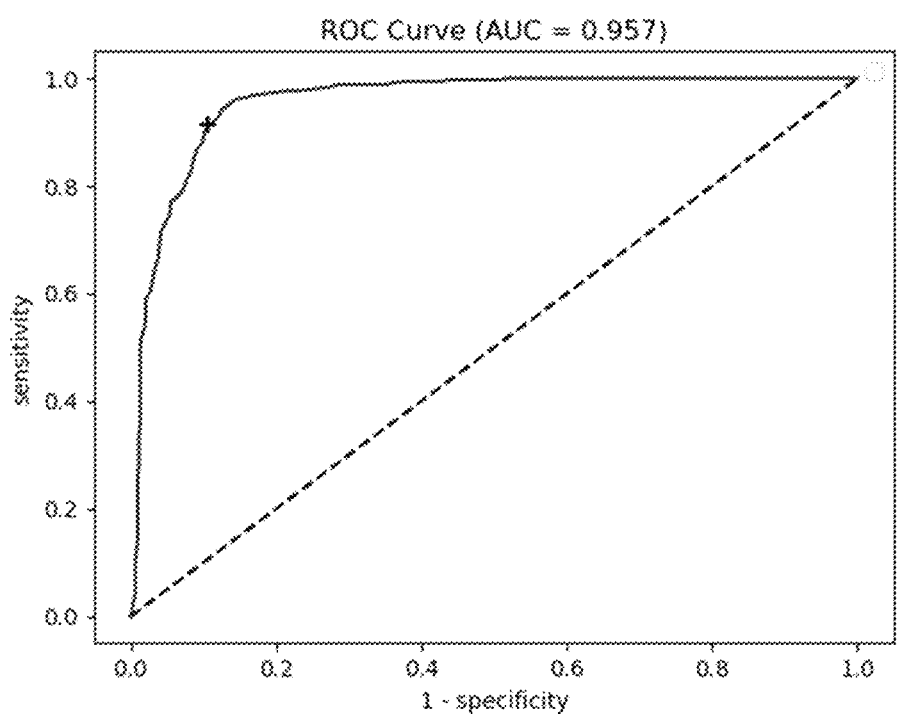
FIG. 3: Receiver operating characteristic (ROC) curve from the comparison of the outputs of an NN-based algorithm to the experts' evaluation on the tuning subset, so as to validate the digital video classifier.

The present invention presents a device for producing a "digital video classifier" in order to determine the quality of cleanliness of one or more segments of the digestive tube in a video capsule endoscopy (VCE) of a subject.

The device can comprise:
- a VCE allowing the acquisition of videos of segments of the digestive tube,
- video storage means, coupled with the VCE,
- an "image database" with images extracted from VCE exams and classified during a step so-called "image ground truth": into images with "adequate" cleanliness and images with "non-adequate" cleanliness; according to a score, determined by a visual analysis of the images, based on at least one medical criteria, and/or
- a "video database" with videos (for instance at least 100 videos) extracted from VCE exams classified during a step so-called "video ground truth": in videos with "adequate" cleanliness and in videos with "non-adequate" cleanliness; according to a score, determined by a visual analysis of the videos, based on at least one medical criteria.

The medical criteria can be elaborated from the following items: the percentage of mucosa visualized, luminosity, the presence of bubbles, the presence of bile/chyme, the presence of liquids and undigested debris.

The device can also comprise computing means connected to the video storage means, and to the databases.

Such computing means, such as one or several processors can be configured for step A) performing a statistical learning for the generation of a "digital image classifier" from the "image database" and which classifies the images in adequate cleanliness or non-adequate cleanliness.

Such computing means can also be configured for step B) generating the "digital video classifier".

In the step (B), the calculating means can be configured to follow the sub-steps:
- a) extraction of all the successive images of each video from the "video database";
- b) automatic classification of the quality of all the successive images from each extracted video, in adequate cleanliness or non-adequate cleanliness, by the "digital image classifier", which realizes a "video cleanliness score" for each video, according to the proportion of images whose quality is in adequate cleanliness;

c) partition of the "video database" into two subsets of videos;

d) calculation of a series of values (sensitivity; 1-specificity), for the plotting of the ROC (receiver operating characteristic) curve, with a step of classification of the videos of the first subset of the "video database" into adequate and non-adequate videos;

e) decision of a desired threshold value between 0% and 100% allowing on the ROC curve to obtain the desired values (sensitivity; 1-specificity) in terms of performance, and/or f) validation of this desired threshold with the calcul of the video cleanliness score on the second subset of videos in the "video database", the value of this validated desired threshold becoming the "digital video classifier" capable of classifying a video of a subject as being of adequate cleanliness or of non-adequate cleanliness of one or more segments (small intestine and/or colon) of the digestive tube as a video capsule endoscopy (VCE).

Advantageously, as represented in FIG. 4, the calculation of a series of values (sensitivity; 1-specificity), in the step d) comprises the following sub-steps:

variation between 0% and 100% (for instance, every 1%), of a threshold value corresponding to the proportion of images beyond which each video is considered adequate, for instance every 1% comparison of each given threshold value to the video scores automatically calculated in step b) which gives the proportion of images whose quality is in adequate cleanliness, and labeling of each video in this first subset as "adequate cleanliness video" or "not adequate cleanliness video", for each given threshold value, counting the number of False Positives, True Positives, False Negatives and True Negatives in the videos of the first subset, by comparison with the classification of videos during the "truth field video" phase as "adequate cleanliness video" or "non-adequate cleanliness video", to determine the associated values (sensitivity, 1-specificity) associated with the given threshold value, the set of values obtained for each threshold value allowing to plot the ROC curve relative to the video classification method on the "test" video database.

Advantageously, the step f) comprises the following sub-steps:

for the desired threshold in step d), considering the associated value (sensitivity; 1-specificity) obtained with the first subset of videos, Validation of the "digital video classifier" for this given desired threshold, by comparison of the associated value (sensitivity; 1-specificity) with the value (sensitivity; 1-specificity) obtained with the second subset of videos.

Advantageously, the calculating means are configured to perform, in the step (A), statistical learning for the generation of a "digital image classifier" from the "image database" by:

(i) a step of automatic learning according to the technique known as "deep neural networks" on a subset of the "image database" drawn at random (advantageously without handing the images, discounting), allowing the generation of a "digital image classifier", (ii) a test step on the remaining images of the "image database" enabling the specificity and sensitivity of the "digital image classifier" to be validated, by comparison with the classification of these remaining images obtained during the step of "image ground truth".

Advantageously, the validation of the "digital image classifier" is carried out when at least the tested images have a specificity and a sensitivity at least equal to 90% of those determined by the classification of the images realized during the step of "truth field image".

Advantageously, the validation of the "digital video classifier" is realized in the step f), when the variation of the obtained values of sensitivity and specificity is 2% maximum between the second subset of videos and the first subset of videos, for the desired threshold.

Advantageously, the construction of two subsets of the "video database" is realized so as to have the same proportions of adequate cleanliness/non-adequate cleanliness videos according to "truth field video" in the two subsets.

Advantageously, both subsets of the "video database" have the same size.

Advantageously, the value (sensitivity; 1-specificity) corresponds to the "operational point" of the ROC curve.

Advantageously, the value (sensitivity; 1-specificity) corresponds to a sensitivity value of 100% for maximum specificity.

Advantageously, both subsets of the "video database" are produced randomly.

Advantageously, in step (A) learning is realized by a deep neural network architecture of the "Convolutional Neural Network (CNN)" type.

Advantageously, in step (A) learning is achieved by a deep neural network architecture of the "Generative Adversarial Network (GAN)" type.

The present invention concerns also a method for producing the digital video classifier, in order to determine the quality of cleanliness of one or more segments of the digestive tube (small intestine or colon) in a video capsule endoscopy (VCE) and which can use the device as defined above.

Thus, the method can comprise: A) performing a statistical learning for the generation of a "digital image classifier" from the "image database".

The method can comprise B) generating the "digital video classifier" with the "digital image classifier".

In particular, generating the "digital video classifier can comprise the following steps:

a) extraction of all the successive images of each video from the "video database";

b) automatic classification of the quality of all the successive images from each extracted video, in adequate cleanliness or non-adequate cleanliness, by the "digital image classifier", which realizes a "video cleanliness score" for each video, according to the proportion of images whose quality is in adequate cleanliness;

c) partition of the "video database" into two subsets of videos;

d) calculation of a series of values (sensitivity; 1-specificity), for the plotting of the ROC curve, with a step of classification of the videos of the first subset of the "video database" into adequate and non-adequate videos;

e) decision of a desired threshold value between 0% and 100% allowing on the ROC curve to obtain the desired values (sensitivity; 1-specificity) in terms of performance, and/or f) validation of this desired threshold with the calcul of the video cleanliness score on the second subset of videos in the "video database", the value of this validated desired threshold becoming the "digital video classifier" capable of classifying a video of a subject as being of adequate cleanliness or of non-adequate cleanliness of one or more segments of the digestive tube as a video capsule endoscopy (VCE).

The invention presents also a method of control applied to a given video made by video capsule, in at least one segment of the digestive tube of a person, for automatically determining the quality of visualization of the images of the video, using the device's "digital video classifier" as defined above and the video cleanliness score, applied to the images of the given video, to automatically determine, in an automatic screening test, whether the video given is "adequate" or "non-adequate" cleanliness.

The method of control can be applied to different persons, and in that case:
- a preliminary step of intestinal preparation for the control examination, which is different for each person,
- a step of controlling the automatic examination of the video carried out on each person,
- a step of comparing the efficiency of the different intestinal preparations under examination according to the video cleanliness score obtained from each video, determined for each different intestinal preparation by the method of control.

One Embodiment

Methods. The proposed NN-based algorithm used a 16-layer Visual Geometry Group architecture. A database of 600 normal third-generation SBCE still frames was artificially augmented to 3000 frames. These frames were categorized as "adequate" or "non-adequate" in terms of cleanliness by five expert readers, according to a 10-point scale and served as a reference for the training of the algorithm. A second database comprised 156 different third generation SBCE recordings, selected from a previous multicenter randomized controlled trial. These recordings were categorized in a consensual manner by three experts, according to a cleanliness assessment scale, and split into two independent 78-video subsets, to serve as a reference for the tuning and evaluation of the algorithm.

Results. A proportion of 79% still frames per video selected as "adequate" by the algorithm was determined to achieve the best performance. Using this threshold, the algorithm yielded a sensitivity of 90.3%, a specificity of 83.3%, and an accuracy of 89.7%. The reproducibility was optimal (kappa=1.0). The mean calculation time per video was 3±1 minutes.

Conclusion. The present invention allows an automatic and highly sensitive assessment of digestive tube cleanliness during capsule endoscopy and paves the way for automated, standardized SBCE reports.

Materials & Methods

Deep Learning Algorithm

Machine learning (ML) is a type of artificial intelligence (AI) technique that allows the analysis of a large amount of data, such as the content of full-length videos (7,8). ML approaches based on convolutional neural networks (NNs) have already been used in the setting of CE and have demonstrated good performance for the automated detection of SB lesions (9-11).

The proposed NN-based algorithm was trained, tuned, and evaluated using a custom 16-layer Visual Geometry Group architecture (12). The NN-algorithm included convolutional layers at different scales, a ReLu unit and Max-Pool layers for the extraction of features.

Training Dataset for Deep Learning, at the Still Image Level

Six-hundred SBCE frames were first used to train and tune the NN-based algorithm at the still image level. This dataset has been described elsewhere. Briefly, these 600 frames were randomly extracted from 30 normal, complete, deidentified, third-generation SBCE video recordings (Pillcam SB3®, Medtronic, Minneapolis, MN, USA); all 600 frames were analyzed by three experts independently, to assess SB cleanliness, by using the 5-item, 10-point, quantitative index (QI) by Brotz et al. (3).

A still frame was categorized as having adequate cleanliness when the mean score of the three experts' scores was ≥7/10. Data augmentation (flipping and rotation) was used to increase the robustness of the training process. Overall, the data augmentation led us to consider a pool of 3000 images. Receiver operating characteristic (ROC) curves were obtained from the comparison of the outputs of various versions of the NN-based algorithms to the experts' evaluation. The optimal algorithm, which could distinguish adequately from non-adequately clean SB still frames with the highest performance, was selected by computing the operating point of the best-fitting ROC curve.

Tuning and Evaluation Datasets for Deep Learning, at the Video Level

The NN-based algorithm, preliminarily trained and on still frames, was then tuned to categorize videos. For this purpose, we used 156 complete, deidentified, third-generation (Pillcam SB3®), SBCE video recordings from the PREPINTEST multicenter randomized controlled trial (14). The PREPINTEST trial aimed to compare the diagnostic yield of second and third generation SBCE according to three different preparation regimens (ClinicalTricals.gov identifier NCT01267981): standard diet (clear liquids only after lunch the day before, and fasting overnight) vs. standard diet+500 mL of polyethylene-glycol (PEG) purge 30 minutes after SBCE intake vs. standard diet+2000 mL PEG the night before+500 mL PEG 30 minutes after SBCE intake.

The 156 complete third-generation video recordings retrieved from the five most active centers of the PREPINTEST trial were edited in an universal video format (mpeg) from the first to the last SB frame. All the videos were independently reviewed at an accelerated speed (×32) by three expert readers, and categorized as "adequate" or "non-adequate" (in terms of SB cleanliness) using the overall adequacy assessment (OAA) scale (Table 1), as described in the study by Brotz et al. (3).

TABLE 1

Overall adequacy assessment (OAA) and Qualitative evaluation (QE) scale from Brotz et al. (3).

| OAA | QE | Criteria |
|---|---|---|
| Adequate | Excellent | Visualization of ≥90% of mucosa, no, or minimal, fluid and debris, bubbles, and bile/chyme staining; no, or minimal, reduction of brightness |
| | Good | Visualization of ≥90% of mucosa; mild fluid and debris, bubbles, and bile/chyme staining; mildly reduced brightness |
| Inadequate | Fair | Visualization of <90% of mucosa; moderate fluid and debris, bubbles, and bile/chyme staining; moderately reduced brightness |
| | Poor | Visualization of <80% of mucosa; excessive fluid and debris, bubbles, and bile/chyme staining; severely reduced brightness |

Each video deemed "adequate" by two or three experts was considered consensually "adequate", and conversely each video deemed "non-adequate" by two or three experts was considered consensually "non-adequate". The experts' consensual "adequate"/"non-adequate" classification (in terms of cleanliness) was considered the "ground truth" (Table 2).

TABLE 2

Proportion of adequate and inadequate videos (in terms of small bowel cleanliness) in the tuning and evaluation subsets

| Video | Adequate cleanliness | Inadequate cleanliness | Total |
|---|---|---|---|
| Tuning subset | 72 | 6 | 78 |
| Evaluation subset | 72 | 6 | 78 |
| Total | | | 156 |

The 156-video dataset was then randomly split into two 78-video independent subsets (FIG. 1). The selected NN-based algorithm was tuned on the first random subset of 78 videos (tuning subset). ROC curves and their operating points were computed and used to determine the optimal proportion of adequate still frames per video for the best prediction of the experts' consensual classification. The performances of the best-fitting NN-based algorithm were then evaluated on the second random subset of 78 videos (evaluation subset), with the experts' consensual classification ("adequate" vs. "non-adequate") of cleanliness as a reference.

Endpoints

The primary endpoint was the sensitivity (Se) of the algorithm for predicting the adequate cleanliness during SBCE at the video level. The specificity (Sp), positive and negative predictive values (PPV and NPV respectively), reproducibility, and calculation times were considered secondary endpoints. Qualitative data were reported as percentages with 95% confidence intervals (95% C.I.). Quantitative data are reported as means±standard deviations; (SDs). Cohen's kappa was calculated to assess reproducibility.

Results

After data augmentation and initial training on still frames of the SB, the best-fitting NNbased algorithm demonstrated a sensitivity of 91.1% (95% C.I. [88.8%; 93.4%]), a specificity of 90.0% (95% C.I. [83.3%; 96.7%]), and an accuracy of 95.7% (95% C.I. [91.2%; 100.0%])

(FIG. 2).

In the second database, 144 videos out of 156 (93.3%) were categorized by the experts as "adequate" in terms of SB cleanliness. The same proportion (72 out of 78, i.e., 93.3%) of "adequate" SBCE videos in terms of SB cleanliness were randomly distributed into a tuning subset and an evaluation subset (Table 2). The optimal proportion of adequate still frames per video for the best prediction of the experts' consensual classification was 79%

(FIG. 3).

In the evaluation subset (Table 3), 65 videos were categorized as "adequate" (in terms of cleanliness) by the NN-based algorithm among 72 "adequate" videos according to the experts (i.e., true positives), thus providing a sensitivity of 90.3% (95% C.I. [83.7%; 96.9%]).

TABLE 3

Performances of the NN-based algorithm outputs for the assessment of SB cleanliness, compared to the consensual

| | | Algorithm output | | |
|---|---|---|---|---|
| Videos | | Adequate | Inadequate | Total |
| Experts* consensual evaluation | Adequate | 65 | 7 | 72 |
| | Inadequate | 1 | 5 | 6 |
| Total | | 66 | 12 | 78 |

Conversely, 5 videos were categorized as "non-adequate" among 6 "non-adequate" videos according to the experts (i.e., true negatives) yielding a specificity of 83.3% (95% C.I. [75.0%; 91.6%]). The PPV was 98.5% (95% C.I. [95.8%; 100.0%]) and the NPV was 41.7% (95% C.I. [30.8%; 52.6%]). Overall, the diagnostic accuracy was 89.7% (95% C.I. [82.9%; 96.4%]). The reproducibility was perfect (kappa=1.0). The mean calculation time per video was 3±1 minutes.

DISCUSSION

The developed NN-based algorithm allowed the rapid and reproducible automated assessment of the cleanliness of the SB during CE. It was demonstrated to be highly sensitive (Se of 90.3%, and a PPV of 98.5).

The assessment of adequacy of bowel cleansing is listed in the ESGE Quality Improvement Initiative as a performance measure for SBCE (5) and in the Clinical Practice Guidelines of the Canadian Association of Gastroenterology as an appropriate element of good practice (6). SB cleanliness should therefore be included in all CE reports. However, SBCE preparation scales have poor reproducibility (3). Although among the most popular scores in this setting, the scores proposed by Brotz et al. had interobserver reproducibility coefficients varying between 0.41 and 0.47 (5). Thus, a quality initiative process of the ESGE and UEG has recently emphasized that "The development/identification of a single, universally accepted, validated scale, as well as the development of software for assessment of the quality of SB preparation, would allow standardized evaluation and monitoring of this performance measure". (5)

Previous studies have demonstrated the high diagnostic performances of handcrafted computerized algorithms at assessing SB quality preparation in CE still frames, by calculating the red-on-green ratio, the abundance of bubbles, the frames brightness and the ratio of color intensities of the red and green channel available on the tissue color bar of the reading software (15). It has since been demonstrated that NN-based algorithms can significantly reduce the time for detecting gastrointestinal lesions in SBCE recordings (9-11, 16), but they have not yet been used to rate the cleanliness of the SB. Our work demonstrates a valuable tool to be implemented in daily clinical practice, especially in CE reports for better standardization and quality reporting.

The present study has many strengths. First, the tuning and evaluation databases came from a multicenter trial (14) that randomized patients to three different bowel preparations, thus offering some variability in SB cleanliness in the recordings. Second, a consensual classification by three expert readers provided a strong asset for the assessment of SB cleanliness.

CONCLUSION

A NN-based algorithm allowing the automatic assessment of cleanliness of the SB during CE was demonstrated to be rapid, reproducible and highly sensitive. This invention, paves the way for automated, standardized SBCE reports. This NN-based algorithm will also allow valid comparisons of different preparation regimens, in terms of cleanliness, and in terms of CE diagnostic yield according to cleanliness.

REFERENCES

1. Iddan G, Meron G, Glukhovsky A, Swain P. Wireless capsule endoscopy. Nature. 2000; 25; 405(6785):417.
2. Niv Y. Efficiency of bowel preparation for capsule endoscopy examination: a meta-analysis. World J Gastroenterol. 2008; 7; 14(9):1313-7.
3. Brotz C, Nandi N, Conn M, Daskalakis C, DiMarino M, Infantolino A, et al. A validation study of 3 grading systems to evaluate small-bowel cleansing for wireless capsule endoscopy: a quantitative index, a qualitative evaluation, and an overall adequacy assessment. Gastrointest Endosc. 2009; 69(2):262-70, 270.e1.
4. Le Mouel J P, Houist G, Saurin J C et al. Cleanliness scores for small bowel capsule endoscopy: an external (un)validation study. United Eur Gastroenterol Journal Volume 7 Issue 8 (Supplement), 2019.
5. Spada C, McNamara D, Despott E J, Adler S, Cash B D, Fernandez-Urion I, et al. Performance measures for small-bowel endoscopy: A European Society of Gastrointestinal Endoscopy (ESGE) Quality Improvement Initiative. United Eur Gastroenterol J. 2019; 7(5):614-41.
6. Enns R A, Hookey L, Armstrong D, Bernstein C N, Heitman S J, Teshima C, et al. Clinical Practice Guidelines for the Use of Video Capsule Endoscopy. Gastroenterology. 2017; 152(3):497-514.
7. Le Berre C, Sandborn W J, Aridhi S, Devignes M-D, Fournier L, Small-Tabbone M, et al. Application of Artificial Intelligence to Gastroenterology and Hepatology. Gastroenterology. 2020; 158(1):76-94.e2.
8. Rajkomar A, Dean J, Kohane I. Machine Learning in Medicine. N Engl J Med. 2019 04; 380(14):1347-58.
9. Ding Z, Shi H, Zhang H, Meng L, Fan M, Han C, et al. Gastroenterologist-level Identification of Small Bowel Diseases and Normal Variants by Capsule Endoscopy Using a Deep-learning Model. Gastroenterology. 2019;
10. Leenhardt R, Vasseur P, Li C, Saurin J C, Rahmi G, Cholet F, et al. A neural network algorithm for detection of GI angiectasia during small-bowel capsule endoscopy. Gastrointest Endosc. 2019; 89(1):189-94.
11. Aoki T, Yamada A, Aoyama K, Saito H, Tsuboi A, Nakada A, et al. Automatic detection of erosions and ulcerations in wireless capsule endoscopy images based on a deep convolutional neural network. Gastrointest Endosc. 2019; 89(2):357-363.e2.
12. Simonyan K, Zisserman A. Very deep convolutional networks for large-scale image recognition. arXiv preprint arXiv:1409.1556, 2014.
14. Cholet F., Rahmi G., Gaudric M et al. Does polyethylene glycol cleansing purge improve video capsule endoscopy diagnostic yield in obscure gastrointestinal bleeding. Endoscopy. 2018; 50:S18. 4.
15. Van Weyenberg S J B, De Leest H T J I, Mulder C J J. Description of a novel grading system to assess the quality of bowel preparation in video capsule endoscopy. Endoscopy. 2011; 43(5):406-11.
16. Saito H, Aoki T, Aoyama K, Kato Y, Tsuboi A, Yamada A, et al. Automatic detection and classification of protruding lesions in wireless capsule endoscopy images based on a deep convolutional neural network. Gastrointest Endosc. 2020;
17. Lapalus M-G, Ben Soussan E, Saurin J-C, Favre O, D'Halluin P N, Coumaros D, et al. Capsule endoscopy and bowel preparation with oral sodium phosphate: a prospective randomized controlled trial. Gastrointest Endosc. 2008; 67(7):1091-6.

The invention claimed is:

1. A device for producing a digital video classifier configured to determine a quality of cleanliness of one or more segments of a digestive tube of a subject from a capsule endoscopy video of the subject digestive tube, comprising:
a data storage medium configured to store:
an image database with images extracted from video capsule endoscopy-VCE-exams and categorized into predetermined images categories including images with adequate cleanliness and images with non-adequate cleanliness; said predetermined image categories referring to a score determined by a visual analysis of the images based on at least one medical criterion, and
a video database with videos extracted from VCE exams categorized into predetermined video categories including videos with adequate cleanliness and videos with non-adequate cleanliness; said predetermined video categories referring to a score determined by a visual analysis of the videos, based on at least one medical criterion,
the at least one medical criterion being selected from: percentage of mucosa visualized, luminosity, presence of bubbles, presence of bile/chyme, presence of liquids and/or undigested debris,
one or several processors connected to the data storage medium, and configured for:
(A) performing a statistical learning for generation of a digital image classifier from the image database and which classifies the images in adequate cleanliness or non-adequate cleanliness;
(B) generating the digital video classifier, by the following steps:
a) extraction of all the successive images of each video from the video database;
b) automatic classification of the quality of all the successive images from each extracted video, in adequate cleanliness or non-adequate cleanliness, by the digital image classifier, and computing a video cleanliness score for each video according to a proportion of images whose quality is of adequate cleanliness;
c) automatic classifications of the videos into videos with adequate cleanliness and videos with non-adequate cleanliness, each of said classifications of the videos being done with one of a plurality of threshold values applied to the video cleanliness score;
d) computing a plurality of receiver operating characteristics-ROC-for each of the automatic classifications of the videos according to the predetermined video categories;
e) computing of a desired threshold value between 0% and 100% of the video cleanliness score allowing to obtain desired values in terms of ROC performance, and
f) validating the desired threshold of the video cleanliness score with a further set of videos from the video database, wherein the validation of said desired threshold comprises comparison of the receiver operating characteristic such as values of sensitivity and specificity obtained with a first subset of videos from the further set of videos with the receiver operating characteristic obtained with a second subset of videos from the further set of videos,
the digital video classifier being validated in step (f) when a variation of obtained receiver operating characteristic such as values of sensitivity and specificity is 2% maximum between the second subset of videos and the first subset of videos, for the desired threshold,
the value of this desired threshold of the video cleanliness score becoming, in combination with the digital image classifier, the digital video classifier capable of classifying a video of one or more segments of a subject digestive tube as being of adequate cleanliness or of non-adequate cleanliness.

2. The device for producing a digital video classifier according to claim 1, wherein in step f) the two subsets of videos the video database are selected so as to have the same proportions of adequate cleanliness/non-adequate cleanliness videos according to the predetermined video categories.

3. The device for producing a digital video classifier according to claim 1, wherein the computing a plurality of ROCs in the steps c) and d) comprises the following sub-steps:
variation between 0% and 100%, of the plurality of threshold values applied to the video cleanliness score corresponding to the proportion of images beyond which each video is considered adequate,
labeling of each video in a subset as adequate cleanliness video or not adequate cleanliness video depending on the threshold values,
for each given threshold value, counting a number of False Positives, True Positives, False Negatives and True Negatives in the videos of the first subset, by comparison of the video labels with the predetermined videos categories, to determine associated values of receiver operating characteristic associated with the given threshold value, and
plotting a ROC curve from the set of values obtained for each threshold value.

4. The device for producing a digital video classifier according to claim 1, wherein the receiver operating characteristics includes true positive rate and false positive rate at various threshold settings.

5. The device for producing a digital video classifier according to claim 1, wherein in step (A) learning is realized by a deep neural network architecture of the Convolutional Neural Network (CNN) type or of the Generative Adversarial Network (GAN) type.

6. The device for producing a digital video classifier according to claim 5, wherein the calculating means perform, in the step (A), a statistical learning for the generation of the digital image classifier from the image database further comprising:
(i) a step of automatic learning according to a technique known as "deep neural networks" on a subset of the image database drawn at random, allowing the generation of a digital image classifier, and
(ii) a test step on the remaining images of the image database enabling specificity and sensitivity of the digital image classifier to be validated, by comparison of the automatic classification with the predetermined image categories of these remaining images.

7. The device for producing a digital video classifier according to claim 6, wherein the digital image classifier is validated when at least the tested images have a specificity and a sensitivity at least equal to 90% compared to the predetermined image categories.

8. A method for producing a digital video classifier configured to determine a quality of cleanliness of one or more segments of a digestive tube of a subject from a capsule endoscopy video of the subject digestive tube, said method being executed by one or several processors connected to a data storage medium configured to store:
an image database with images extracted from video capsule endoscopy-VCE-exams and categorized into predetermined images categories including images with adequate cleanliness and images with non-adequate cleanliness; said predetermined image categories referring to a score determined by a visual analysis of the images based on at least one medical criterion, and
a video database with videos extracted from VCE exams categorized into predetermined video categories including videos with adequate cleanliness and videos with non-adequate cleanliness; said predetermined video categories referring to a score determined by a visual analysis of the videos, based on at least one medical criterion,
the at least one medical criterion being selected from: percentage of mucosa visualized, luminosity, presence of bubbles, presence of bile/chyme, presence of liquids and/or undigested debris,
said method comprising the following steps:
(A) performing a statistical learning for the generation of a "digital image classifier" from the "image database" and which classifies the images in adequate cleanliness or non-adequate cleanliness;
(B) generating the digital video classifier, by the following steps:
a) extraction of all the successive images of each video from the video database;
b) automatic classification of the quality of all the successive images from each extracted video, in adequate cleanliness or non-adequate cleanliness, by the digital image classifier, and computing a video cleanliness score for each video according to a proportion of images whose quality is of adequate cleanliness;
c) automatic classifications of the videos into video with adequate cleanliness and videos with non-adequate cleanliness, each of said classifications of the videos being done with one of a plurality of threshold values applied to the video cleanliness score;
d) computing a plurality of receiver operating characteristic-ROC-for each of the automatic classifications of the videos according to the predetermined video categories;
e) computing of a desired threshold value between 0% and 100% of the video cleanliness score allowing to obtain desired values in terms of ROC performance,
f) validating the desired threshold of the video cleanliness score with a further set of videos from the video database, wherein the validation of said desired threshold comprises comparison of the receiver operating characteristic such as values of sensitivity and specificity obtained with a first subset of videos from the further set of videos with the receiver operating characteristic obtained with a second subset of videos from the further set of videos, the digital video classifier being validated in step (f) when a variation of obtained receiver operating characteristic such as values of sensitivity and specificity is 2% maximum between the second subset of videos and the first subset of videos, for the desired threshold, the value of this desired threshold of the video cleanliness score becoming, in combination with the digital image classifier, the digital video classifier capable of classifying a video of one or more segments of a subject digestive tube as being of adequate cleanliness or of non-adequate cleanliness.

9. The method for producing a digital video classifier according to claim 8, wherein the steps c) and d) comprise the following sub-steps:

variation between 0% and 100%, of the plurality of threshold values applied to the video cleanliness score corresponding to the proportion of images beyond which each video is considered adequate, labeling of each video in a subset as adequate cleanliness video or not adequate cleanliness video depending on the threshold values, for each given threshold value, counting a number of False Positives, True Positives, False Negatives and True Negatives in the videos of the first subset, by comparison of the video labels with the predetermined videos categories, to determine associated values of receiver operating characteristic associated with the given threshold value, and plotting a ROC curve from the set of values obtained for each threshold value.

10. The method for producing a digital video classifier according to claim 8, further comprising:

a step of automatic learning according to the technique known as "deep neural networks" on a subset of the image database drawn at random, allowing the generation of a digital image classifier, a test step on the remaining images of the image database enabling the specificity and sensitivity of the digital image classifier to be validated, by comparison with the predetermined image categories of these images.

11. The method for producing a digital video classifier according to claim 8, wherein in step (A) learning is realized by a deep neural network architecture of the "Convolutional Neural Network (CNN)" type or of the "Generative Adversarial Network (GAN)" type.

12. A method of control applied to a given video made by video capsule, in at least one segment of a digestive tube of a person, for automatically determining a quality of visualization of images of the video, said method using the digital video classifier, produced according to the method of claim 8, to the given video, to automatically determine, in an automatic screening test, whether the video given is of adequate or non-adequate cleanliness.

13. The method of control according to claim 12, applied to different persons, further comprising:

a preliminary step of non-chirurgical intestinal preparation for a control examination, which is different for each person, a step of controlling automatic examination of the video carried out on each person, and a step of comparing efficiency of the different intestinal preparations under examination according to the video cleanliness score obtained from each video, determined for each different intestinal preparation by the method of control.

14. A device for the automated assessment of small bowel cleanliness based on capsule endoscopy video, said device comprising one or several processor configured to apply the digital video classifier produced according to the method according to claim 8, to a given video made by endoscopy video capsule, and to automatically determine whether the video given is of adequate or non-adequate cleanliness.

* * * * *